(12) United States Patent
McAllister

(10) Patent No.: US 8,734,395 B2
(45) Date of Patent: May 27, 2014

(54) MICRONEEDLE PATCH APPLICATOR

(71) Applicant: Valeritas, Inc., Bridgewater, NJ (US)

(72) Inventor: Devin V. McAllister, Marietta, GA (US)

(73) Assignee: Valeritas, Inc., Bridgewater, NJ (US)

( * ) Notice: Subject to any disclaimer, the term of this patent is extended or adjusted under 35 U.S.C. 154(b) by 0 days.

(21) Appl. No.: 13/972,442

(22) Filed: Aug. 21, 2013

(65) Prior Publication Data

US 2013/0338596 A1 Dec. 19, 2013

Related U.S. Application Data

(63) Continuation of application No. 13/332,065, filed on Dec. 20, 2011, now Pat. No. 8,540,672.

(60) Provisional application No. 61/426,199, filed on Dec. 22, 2010.

(51) Int. Cl.
*A61M 5/20* (2006.01)
*A61M 37/00* (2006.01)
*A61B 19/02* (2006.01)
*A61B 17/20* (2006.01)

(52) U.S. Cl.
CPC ... *A61M 37/0015* (2013.01); *A61M 2037/0023* (2013.01); *A61B 19/026* (2013.01); *A61B 17/205* (2013.01)
USPC .......................................... 604/136

(58) Field of Classification Search
USPC ......................................... 604/136
See application file for complete search history.

(56) References Cited

U.S. PATENT DOCUMENTS

| 8,540,672 | B2 | 9/2013 | McAllister |
| 2002/0091357 | A1 | 7/2002 | Trautman et al. |
| 2003/0125676 | A1* | 7/2003 | Swenson et al. ............. 604/263 |
| 2004/0087893 | A1 | 5/2004 | Kwon |
| 2007/0027427 | A1 | 2/2007 | Trautman et al. |
| 2007/0078414 | A1 | 4/2007 | McAllister et al. |
| 2008/0208146 | A1* | 8/2008 | Brandwein et al. ........... 604/272 |

(Continued)

FOREIGN PATENT DOCUMENTS

| WO | WO 2007/019539 | 2/2007 |
| WO | WO 2012/088154 | 6/2012 |

OTHER PUBLICATIONS

International Search Report for International Application PCT/US2011/066248, dated Apr. 13, 2012.

(Continued)

*Primary Examiner* — Jason Flick
(74) *Attorney, Agent, or Firm* — Morse, Barnes-Brown & Pendleton, P.C.; Sean D. Detweiler, Esq.

(57) ABSTRACT

A method and apparatus for application of a microneedle patch to a skin surface of a patient includes use of an applicator. The applicator includes a housing, a slidably disposed applicator plate, and a compression spring. The applicator plate is moveable between a retracted position and a deployed position, and has an engaging surface suitable for mashing up against a microneedle patch and pressing it against a skin surface. A docking system transfers the microneedle patch from a support to the applicator without requiring a user to handle the microneedle patch directly. Once mounted in the applicator, the microneedle patch is deployed against a skin surface of a patient for delivery of a desired agent via a microneedle array contained on the patch.

8 Claims, 7 Drawing Sheets

(56) References Cited

U.S. PATENT DOCUMENTS

| | | |
|---|---|---|
| 2009/0187160 A1 | 7/2009 | McAllister et al. |
| 2010/0121271 A1 | 5/2010 | Perriere |
| 2010/0152701 A1 | 6/2010 | McAllister et al. |

OTHER PUBLICATIONS

Notice of Allowance for U.S. Appl. No. 13/332,065, mailed Jul. 11, 2013.

Non-Final Office Action for U.S. Appl. No. 13/972,460, mailed Mar. 12, 2014.

* cited by examiner

MICRONEEDLE PATCH APPLICATOR

RELATED APPLICATIONS

This application is a continuation of co-pending U.S. patent application Ser. No. 13/332,065, filed Dec. 20, 2011, which claims priority to, and the benefit of, U.S. Provisional Application No. 61/426,199, filed Dec. 22, 2010, for all subject matter common to both applications. The disclosures of said applications are hereby incorporated by reference herein.

FIELD OF THE INVENTION

The present invention relates to a system suitable for protecting a microneedle patch and applying the microneedle patch to a skin surface, and more particularly to a system enabling storage of a microneedle patch in a sterile packaging and transfer and deployment of the patch to a skin surface for delivery of an agent.

BACKGROUND

Microneedle patch technology enables drug delivery into the epidermal and/or dermal layers of the skin. The technology is capable of delivering drugs of different types, size, structure, or charge. Microneedle patches can be applied to patients regardless of their skin characteristics. The patches are optimized to penetrate the shallow layers of the skin, avoiding pain receptors, and to deliver their drug payloads.

Application of microneedle patches can be difficult. The patches can be very small and thus challenging for a patient to handle without damaging and/or contaminating the microneedles prior to application to the skin. Furthermore, microneedle patches must be applied to the skin with a sufficient impact to ensure that the microneedles penetrate the skin to a required degree for the intended drug delivery to occur. This presents additional challenges to patients using the patches, particularly in self-delivery situations.

SUMMARY

There is a need for a microneedle patch applicator system that can reduce or eliminate the potential for damage and/or contamination of the microneedle patch due to handling by a patient or user, while also ensuring the application of the microneedle patch to the skin surface is effected in accordance with the design parameters for skin penetration and drug delivery, and in a consistently repeatable manner. The present invention is directed toward further solutions to address this need, in addition to having other desirable characteristics.

In accordance with example embodiments of the present invention, a microneedle patch applicator includes a housing. A slidably disposed applicator plate, moveable between a retracted position and a deployed position in a reciprocating manner, includes an engaging surface. A compression spring can mount in such a way that imparts a spring force to the applicator plate when the applicator plate is in the retracted position. A microneedle patch docking mechanism can be configured in such a way that the docking mechanism captures and holds a microneedle patch in a position proximal the engaging surface of the applicator plate while the applicator plate is in the retracted position. A latch mechanism can be included that when latched holds the applicator plate in place and when unlatched permits the applicator plate to move. The applicator plate can be placed in the retracted position with the docking mechanism holding the microneedle patch proximal the engaging surface, and when the latch mechanism is unlatched, the applicator plate can be propelled by the compression spring to the deployed position.

In accordance with aspects of the present invention, a trigger mechanism can be included, configured in such a way that activation of the trigger unlatches the latch mechanism. The latch mechanism can be in an unlatched position, enabling the applicator plate to be capable of retraction to the retracted position in response to a force applied to the microneedle patch applicator. Unlatching of the latch mechanism when the applicator plate is in the retracted position can release the applicator plate enabling movement from the retracted position to the deployed position with a kinetic energy of between about 0.1 lbf*in and about 10 lbf*in, and preferably between about 1 lbf*in and about 2 lbf*in.

In accordance with further aspects of the present invention, the compression spring can have a spring constant of between about 0.1 lbf/in and about 50 lbf/in, and preferably between about 2.4 and about 8.5 lbf/in. The microneedle patch applicator can deploy the microneedle patch with sufficient force to anchor the microneedle patch to a skin surface with a plurality of microneedles disposed thereon. The microneedle patch applicator can be stored in a sterile packaging prior to use.

In accordance with example embodiments of the present invention, a microneedle patch support can include a housing having a perimeter defining an internal area. An elevated hub can be disposed within the internal area. The microneedle patch support can be sized and dimensioned to support a microneedle patch in such a way that the microneedle patch rests on the elevated hub, and any needles extending from the microneedle patch do not make contact with the microneedle patch support.

In accordance with aspects of the present invention, the perimeter defining the internal area can be substantially circular in shape. The elevated hub can be disposed at a location that is substantially at a center point of the internal area. The elevated hub can include a substantially mesa shape with a hollow center at a substantially flat portion of a top of the elevated hub. The elevated hub can have a hollow center.

In accordance with example embodiments of the present invention, a microneedle patch applicator system includes an applicator having a housing. A slidably disposed applicator plate, moveable between a retracted position and a deployed position in a reciprocating manner, can have an engaging surface. A compression spring can be mounted in such a way that imparts a spring force to the applicator plate when the applicator plate is in the retracted position. A microneedle patch docking mechanism can be configured in such a way that the docking mechanism captures and holds a microneedle patch in a position proximal the engaging surface of the applicator plate while the applicator plate is in the retracted position. A latch mechanism can be provided that when latched holds the applicator plate in place and when unlatched permits the applicator plate to move. The microneedle patch can be disposed on a support. Upon placement of the applicator onto the microneedle patch and the support, application of force to the applicator can cause retraction of the applicator plate to the retracted position and capture of the microneedle patch by the docking mechanism.

In accordance with aspects of the present invention, a trigger mechanism can be configured in such a way that activation of the trigger unlatches the latch mechanism. When the latch mechanism is in an unlatched position, the applicator plate can be capable of retraction to the retracted position in response to a force applied to the applicator. Unlatching of the latch mechanism when the applicator plate is in the retracted position can release the applicator plate enabling movement from the retracted position to the deployed position with a kinetic energy of between about 0.1 lbf*in and about 10 lbf*in, and preferably between about 1 and about 2 lbf*in.

In accordance with aspects of the present invention, the applicator can deploy the microneedle patch with sufficient force to anchor the microneedle patch to a skin surface with a plurality of microneedles disposed thereon. The microneedle patch can include a plurality of microneedles configured for anchoring the microneedle patch to a skin surface. The microneedle patch can include a plurality of microneedles configured to contain and deliver a bioactive agent upon attaching to a skin surface. The microneedle patch can be stored in a sterile packaging prior to use in the applicator. The microneedle patch can be stored together with the support in a sterile packaging prior to use of the microneedle patch in the applicator. The microneedle patch can contain one or more bioactive agents disposed thereon. The support can include a perimeter defining an internal area. An elevated hub can be disposed at a location that is substantially at a center point of the internal area. The elevated hub can include a substantially mesa shape with a hollow center at a substantially flat portion of a top of the elevated hub. The elevated hub can have a hollow center.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
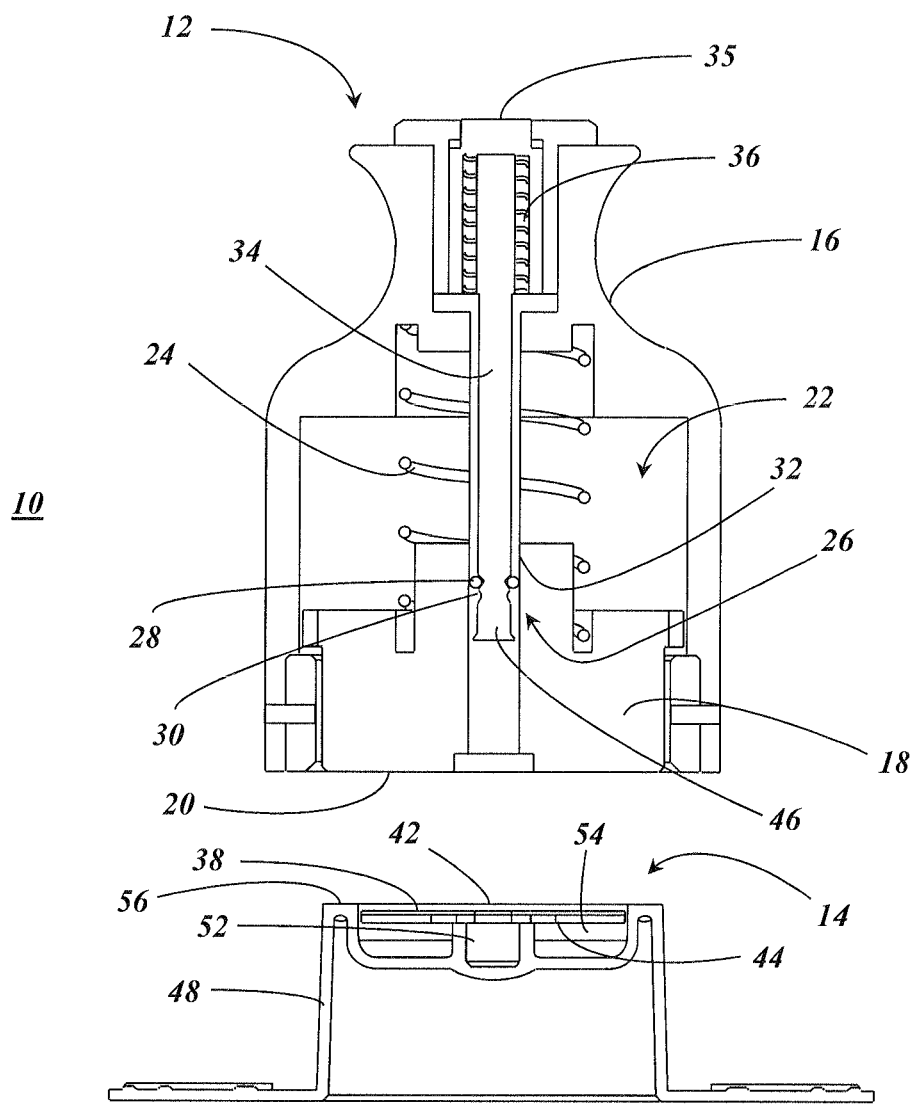
FIG. 1 is a cross-sectional view of a microneedle patch applicator system, according to one aspect of the present invention.

An illustrative embodiment of the present invention relates to a microneedle patch applicator system. The system includes an applicator. The applicator includes a housing, a slidably disposed applicator plate, and a compression spring. The applicator plate is moveable (e.g., slidable) between a retracted position and a deployed position, and has an engaging surface suitable for mashing up against a microneedle patch and impacting it against a skin surface. The compression spring mounts within the applicator in such a way that the spring imparts a spring force to the applicator plate when the applicator plate is in the retracted position. The applicator further includes a microneedle patch docking mechanism configured to capture a microneedle patch, and a latch mechanism that when latched holds the applicator plate in place. The microneedle patch applicator system further includes a microneedle patch disposed on a support. Upon placement of the applicator onto the microneedle patch and support, application of force to the applicator causes retraction of the applicator plate to the retracted position and capture of the microneedle patch by the docking mechanism. At this juncture, the applicator is then placed on a skin surface of a patient and the latch mechanism is unlatched, releasing the spring force to move the applicator plate and the microneedle patch rapidly against the skin surface. Upon impact of the applicator plate and the microneedle patch against the skin surface, microneedles of the microneedle patch are driven into the skin surface, anchoring the microneedle patch to the skin surface and initiating the agent delivery. The compression spring may continue to impart a spring force against the applicator plate while in the deployed position to hold the microneedle patch against the skin surface.

FIGS. 1 through 5, wherein like parts are designated by like reference numerals throughout, illustrate an example embodiment of a microneedle patch applicator system according to the present invention. Although the present invention will be described with reference to the example embodiment illustrated in the figures, it should be understood that many alternative forms can embody the present invention. One of skill in the art will additionally appreciate different ways to alter the parameters of the embodiment disclosed, such as the size, shape, or type of elements or materials, in a manner still in keeping with the spirit and scope of the present invention.

Turning now to FIG. 1, a microneedle patch applicator system 10 is provided in accordance with one example embodiment of the present invention. The system 10 generally includes an applicator 12 and a microneedle patch support 14. The applicator 12 includes a housing 16. The housing 16 provides the structure that supports the components required for the applicator 12. The housing 16 can form an internal chamber 22 in accordance with some embodiments of the present invention. However, an internal chamber 22 is not necessarily required. One function of the internal chamber 22 can be to serve as a guide for the moving components of the applicator 12, as would be understood by one of skill in the art given the present description.

The housing 16 can be formed of a number of different materials, including but not limited to metal, rubber, wood, plastic, composite, synthetic or natural materials, and the like, such that sufficient structural support is provided for the intended use of the applicator 12.

Furthermore, the housing 16 may include a splaying mechanism or feature (not shown) capable of causing the skin of a patient to stretch when the applicator 12 is pressed against the skin, making the skin more receptive of the microneedle patch 38 as delivered by the system 10 of the preset invention. One of skill in the art will appreciate how to implement such a feature.

A slidably disposed applicator plate 18 can be provided, able to move in a reciprocating manner relative to the housing 16. The applicator plate 18 includes an engaging surface 20, and can take a number of different structural forms. The engaging surface 20 is utilized to engage a microneedle patch as described herein. As shown, the engaging surface 20 is a substantially solid planar surface. However, there is no requirement that the engaging surface 20 have this example structure. The microneedle patch 38 as described later herein has one or more needles extending from its surface. The engaging surface 20 need only exist in locations so as to be able to mash up against the back of each microneedle to drive it into the patient's skin as described later herein. The continuous planar surface of the illustrative example reduces the likelihood that a misaligned microneedle patch would not receive the appropriate force at the appropriate location to drive the microneedle as required, but such a continuous planar surface is merely a preferred embodiment, as would be understood by those of skill in the art.

The applicator plate 18, as shown, takes the form of a plunger, capable of sliding movement in a reciprocating manner within the internal chamber 22 of the housing 16. In the illustrative embodiment, the walls of the internal chamber 22 serve to guide the applicator plate 18 in its reciprocating movement within the housing 16.

The applicator plate 18 can be formed of a number of different materials, including but not limited to metal, rubber, wood, plastic, composite, synthetic or natural materials, and the like, such that the applicator plate 18 can operate as intended and described herein.

Figure 4A:
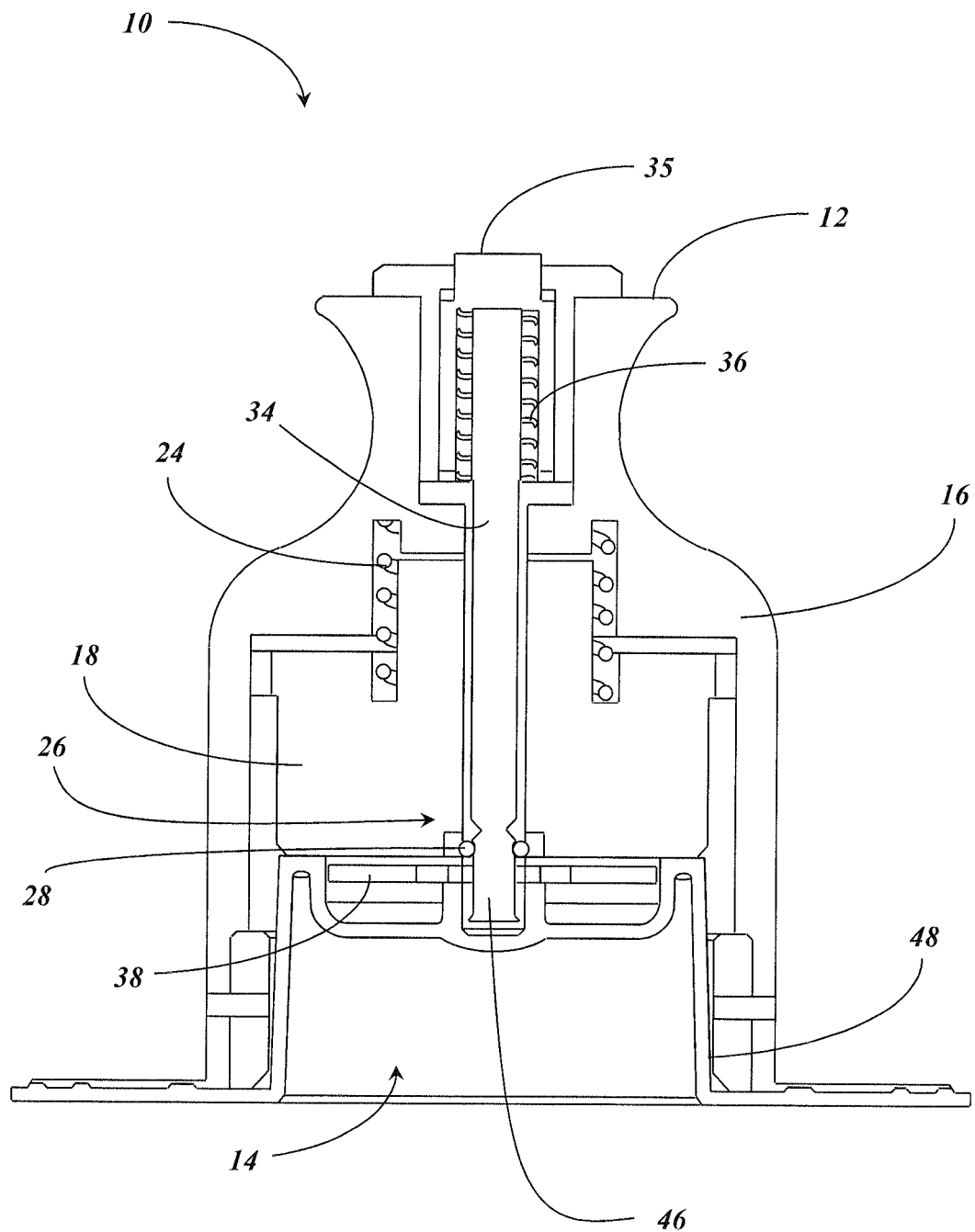
FIG. 4A is a cross-sectional view of the microneedle patch applicator system with an applicator plate in a fully retracted position while the microneedle patch is being loaded, according to one aspect of the present invention.
Figure 4B:
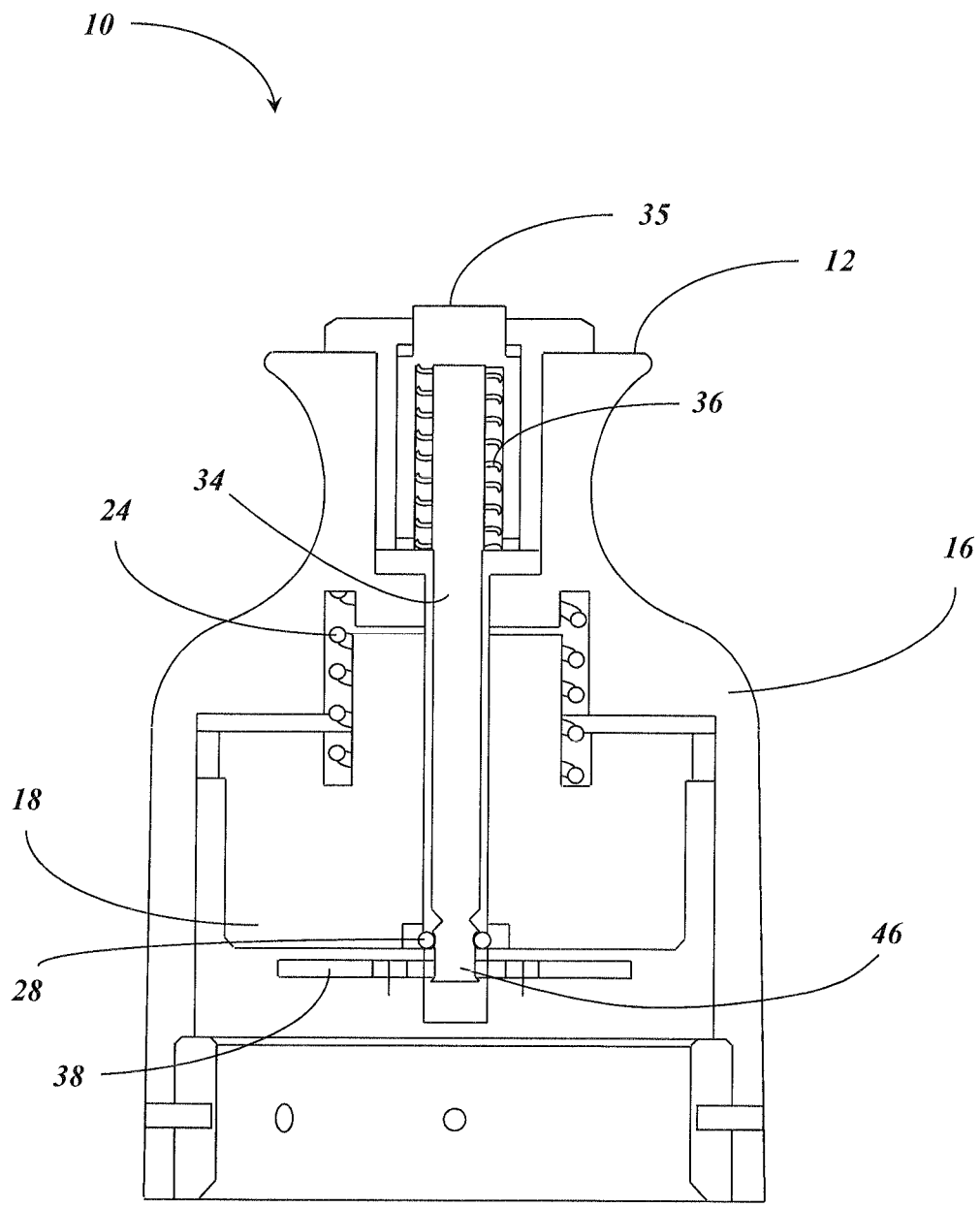
FIG. 4B is a cross-sectional view of the microneedle patch applicator system with the applicator plate in the fully retracted position and the microneedle patch docked or loaded, according to one aspect of the present invention.

The slidably disposed applicator plate 18 is moveable between a retracted position and a deployed position. As shown in FIG. 1, the applicator plate 18 is in a deployed position, demonstrated by the applicator plate 18 being located at a bottom perimeter edge of the housing 16, such that the applicator plate 18 can make contact with a skin surface, or other surface, if the applicator 12 were placed up against such a surface. FIG. 4B shows the applicator plate 18 in a fully retracted position, as will be described later herein. In accordance with one example embodiment of the present invention, the applicator plate 18 can extend slightly beyond the perimeter edge of the housing 16, such that contact with a skin surface of a patient is not hindered by concomitant contact with the perimeter edge of the housing 16.

Figure 4C:
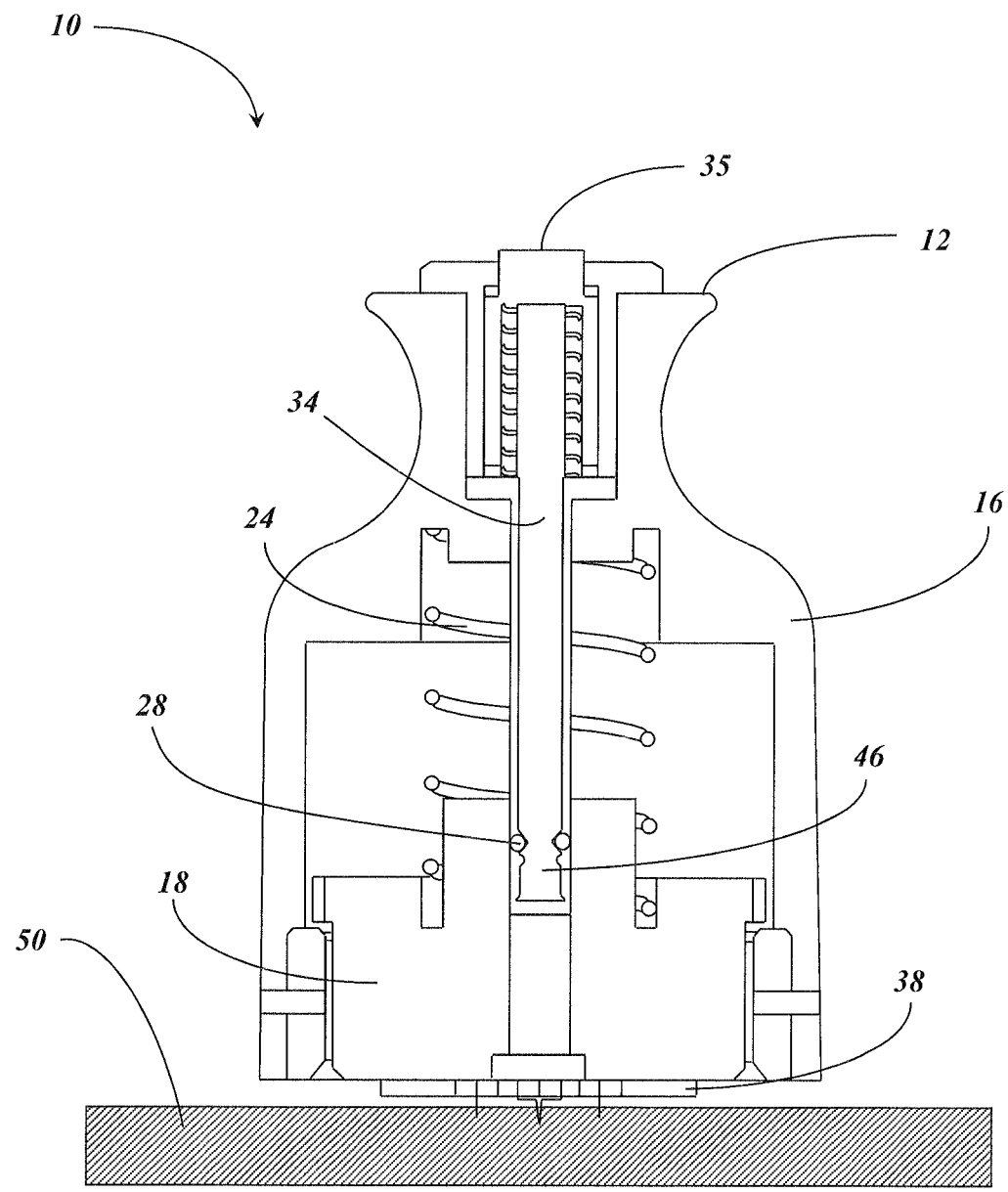
FIG. 4C is a cross-sectional view of the microneedle patch applicator system with the applicator plate in a deployed position and the microneedle patch positioned for transfer to a skin surface, according to one aspect of the present invention.
Figure 5:
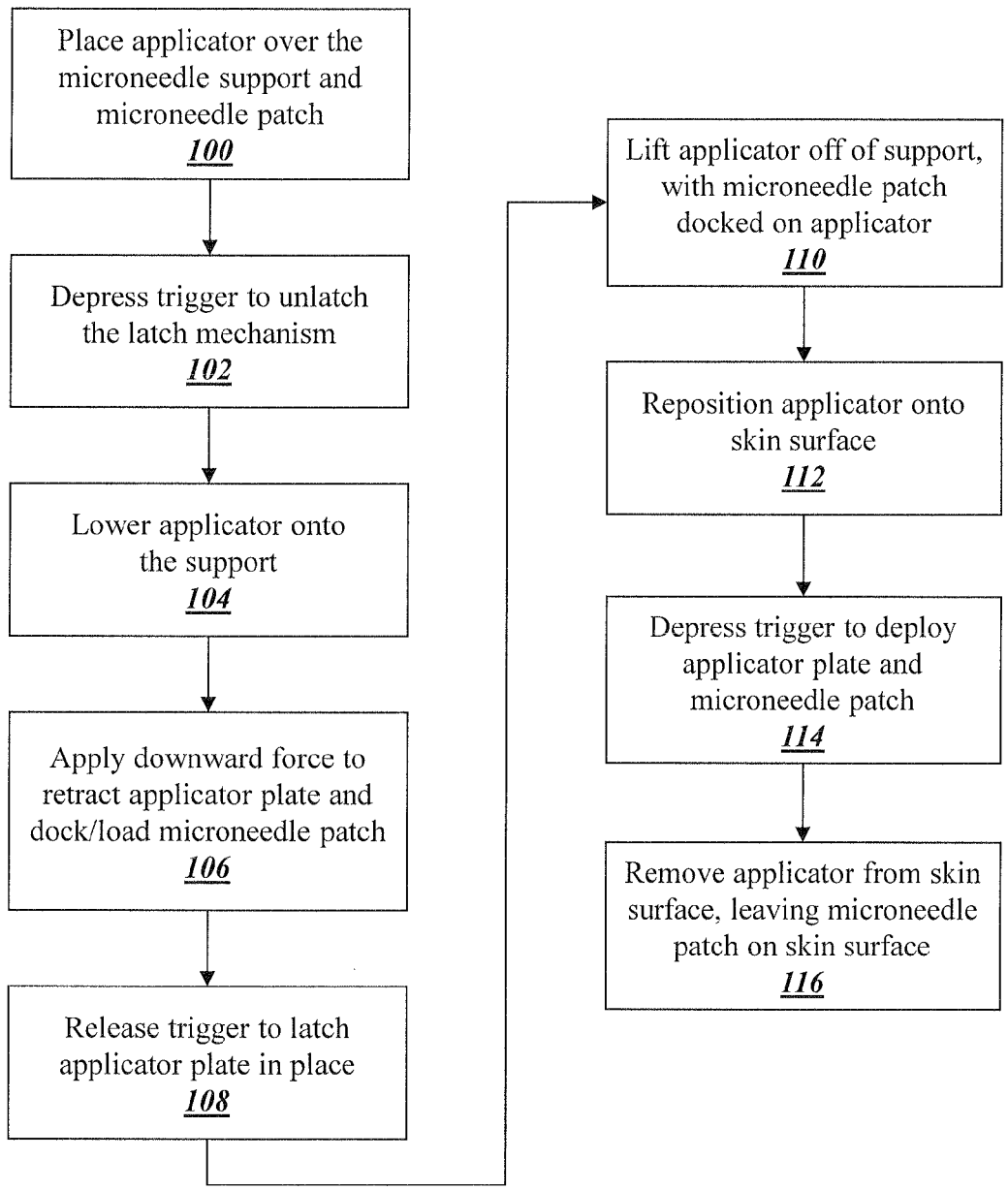
FIG. 5 is a flowchart illustrating a method of loading the microneedle patch applicator with a microneedle patch and deploying the patch on the skin of a patient, according to one aspect of the present invention.

A compression spring 24 is disposed in the applicator 12, mounted in such a way so as to impart a spring force to the applicator plate 18 when the applicator plate 18 is in the retracted position, as described herein. One of skill in the art will appreciate that there are numerous ways of imparting a mechanical spring force to an object. In the present illustrative device, the function of the compression spring 24 is to generate a spring force sufficient to propel the applicator plate 18 from a retracted position (as shown in FIG. 4B) to a deployed position (as shown in FIG. 1, and FIG. 4C) in a manner such that an impact force generated by the slidably disposed applicator plate 18 impacting a skin surface at its deployed position is sufficient to drive a microneedle patch into the skin surface, as described herein. To achieve such a configuration, varying types of springs, spring dimensions, spring characteristics, spring materials, and the like, can be utilized in conjunction with the applicator plate 18 configuration and characteristics to arrive at a desired impact force. Furthermore, different mechanical force translators can be utilized to convey the spring force to the applicator plate 18. Still furthermore, other force generating mechanisms, such as levers, and direct application of force by a user, can be used in conjunction with or as an alternative to the compression spring 24, so long as the functionality of the present invention is maintained. An illustrative example spring suitable for the present application is a spring having a spring constant (k) of about 4.7 lbf/in. In experimental instances of the present invention it was found that springs having a spring constant (k) of 2.4 lbf/in provided an insufficient spring force when utilized with one embodiment of the applicator 12 of the present invention to sufficiently drive the microneedle patch into the skin of a patient. This may have been due to an insufficient compression of the spring. It was further found that a spring having a spring constant (k) of 8.8 lbf/in provided excessive force, such that the resulting impact on the skin of a patient approached an uncomfortable response.

One of skill in the art will appreciate that the present invention is by no means limited to using a compression spring 24 having the specific spring constant (k) provided herein. Rather, one of skill in the art will appreciate that springs having other spring constants (k) may be utilized, so long as they provide a sufficient force with a given spring compression when used with the applicator 12 to drive the microneedle patch into the skin of a patient without causing unnecessary pain or discomfort to the patient. For example, given the results of the example spring constants (k), one of skill in the art may appreciate that a spring having a spring constant (k) of between about 0.1 and 50 lbf/in, and including a more likely range of between about 2.4 lbf/in and 8.5 lbf/in, results in a device having a generally sufficient impact force while not resulting in undue pain or discomfort to the patient. However, these values can change based on various factors specific to intended applications (e.g., age of patient, whether the patient is an animal or a human, etc.) and can be optimized accordingly, as would be appreciated by one of skill in the art. As the spring constant is merely one variable in determining the overall force generated, one of skill in the art will appreciate that the compression spring 24 working in conjunction with the applicator plate 18 should create a stored kinetic energy of about 0.1 to 10 lbf*in, with a preferred range of about 1-2 lbf*in, when in the retracted position, and further should result in an amount of energy dissipated during implementation of the applicator 12 from a retracted position to a deployed position being between about 1-2 lbf*in.

The applicator 12 can further include a latch mechanism 26 or assembly configured to latch or lock the applicator plate 18 in place, preventing sliding movement when such movement is not desired. The latch mechanism 26, in the illustrative embodiment, is formed of a detent 28 able to move between two positions along a stepped indentation 30 of a trigger column 34. As shown in FIG. 1, the detent 28 takes the form of an o-ring that is positioned in a fully receded step of the stepped indentation 30. In this position, the detent 28 does not apply a substantial pressure against an internal wall 32 of a cylindrical aperture that passes through the applicator plate 18 and that contains the latch mechanism 26. As such, the applicator plate 18 is able to move in a reciprocating manner up into the housing 16 and then return to the deployed position. This position of the detent 28 as depicted in FIG. 1 occurs when the trigger column 34 is fully depressed by a user. FIG. 4A shows the applicator plate 18 in a fully retracted position, and also shows the trigger column 34 in a raised position. A trigger spring 36 is configured in such a way that when the trigger column 34 is depressed, a spring force is generated. When the trigger column 34 is released by a user, the spring force of the trigger spring 36 pushes the trigger column 34 upward relative to the applicator plate 18. When the trigger column 34 is in a raised position, the detent 28 slides along the stepped indentation 30 to a less receded step. This action forces the detent 28 radially outward, applying substantial pressure or force to the internal wall 32 of the applicator plate 18 and to the trigger column 34. While in this position, the detent 28 generates sufficient frictional force to prevent the applicator plate 18 from sliding movement, thus locking the applicator plate 18 into place. As shown in FIG. 4A, the applicator plate 18 is in its fully retracted position. The spring force generated by the compression spring 24 is insufficient to overcome the frictional force of the latch mechanism 26 as generated by the detent 28 as positioned in the stepped indentation 30. As such, the applicator plate 18 is locked in place.

Figure 2A:
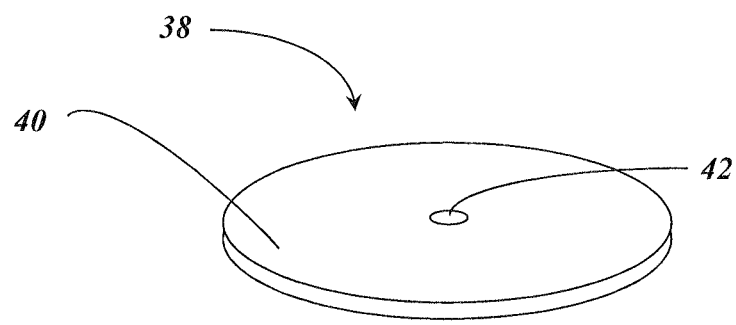
FIG. 2A is a perspective view of a top side of a microneedle patch, according to one aspect of the present invention.
Figure 2B:
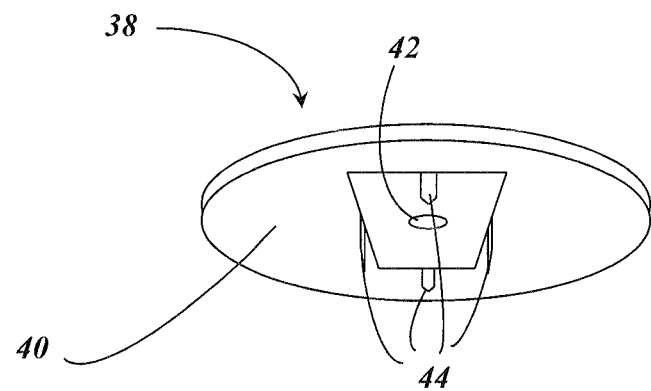
FIG. 2B is a perspective view of a bottom side of the microneedle patch of FIG. 2A, according to one aspect of the present invention.
Figure 3:
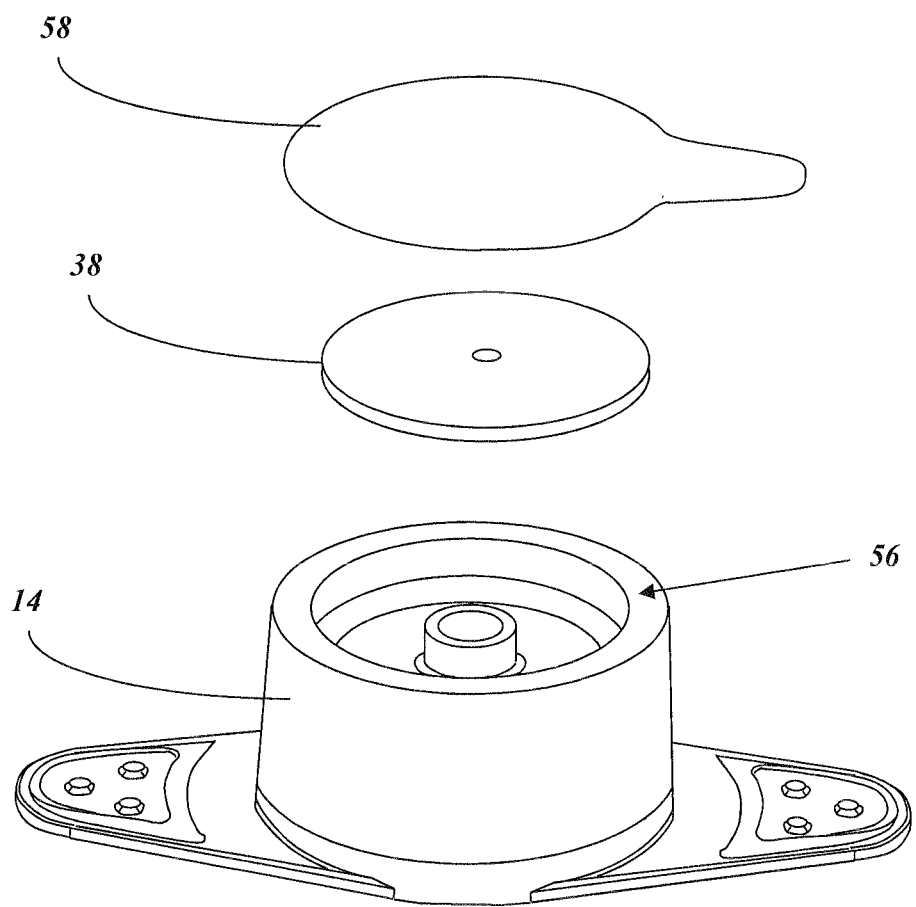
FIG. 3 is an exploded view of the microneedle patch assembled on a support with a sealing cover, according to one aspect of the present invention.

An example microneedle patch 38 suitable for use with the applicator system 10 of the present invention is shown in FIGS. 2A and 2B from a top perspective view and a bottom perspective view, respectively. The microneedle patch 38, as shown, includes a substrate 40 configured in a generally circular (e.g., relatively short cylindrical) shape. The substrate 40 can have any number of shapes, as would be understood by those of skill in the art, so long as they are compatible with the corresponding applicator 12. The substrate 40 includes an aperture 42 passing therethrough, substantially at a center point of the substrate 40. The microneedle patch 38 further includes a microneedle array 44 having a plurality of microneedles coupled with the substrate 40. The microneedle array 44 can contain an agent therein for delivery to the skin of a patient upon the microneedle array 44 penetrating a skin surface 50 of a patient. The term "agent" refers to a single agent or a combination of several agents. The agent may be biologically active or biologically inactive. Sample agents include, without limitation, drugs, vaccines, allergens, antigens, excipients, anti-coagulants, surfactants, radiological dyes or markers, toxins, or any other agent, compound or substance suitable for introduction into a biological environment. As stored, the agent may be, for example, dry (e.g., a film), or in a semi-solid gel. One of skill in the art will appreciate that other agents not listed herein can be utilized in conjunction with the present invention. As such, the present invention is by no means limited to those agents specifically listed herein.

A docking mechanism 46 is configured to capture a microneedle patch 38, as shown in FIG. 1 (see also, FIGS. 4A-4C). In the illustrative embodiment of the present invention, the docking mechanism 46 takes the form of an end section of the trigger column 34. The end section of the trigger column 34 is sized and dimensioned to form an interference fit with the aperture 42 of the microneedle patch 38. As will be described below, the docking mechanism 46 when placed through the aperture 42 of the microneedle patch 38 frictionally couples with the aperture 42, thus docking or loading the microneedle patch 38 onto the applicator 12. One feature of this docking configuration is that the microneedle patch 38 is docked with the applicator 12 in a removable manner. That is, with a force applied to the microneedle patch 38, the microneedle patch 38 will pull away from the docking mechanism 46 of the applicator 12 relatively easily. One of skill in the art will appreciate that a number of alternative docking mechanisms may be utilized to dock or load the microneedle patch 38 onto the applicator 12, such that the present invention is by no means limited to the specific mechanical embodiment described herein. Rather, it is anticipated that other docking mechanisms may be utilized with the applicator 12 of the present invention to provide a removable coupling of the microneedle patch 38 with the applicator 12 in a desired manner. All such equivalent docking mechanisms are anticipated for use with the present invention.

The microneedle patch applicator system 10 further includes a microneedle patch support 14. The microneedle patch support 14 is essentially a base structure capable of supporting the microneedle patch 38 in such a way that the microneedle array 44 is protected from inadvertent contact during storage or handling. In the embodiment illustrated, the microneedle patch support 14 holds the microneedle patch 38 with the microneedle array 44 on an inside facing surface of the microneedle patch 38 (i.e., the surface facing the microneedle patch support 14). The microneedle patch 38 rests on an elevated hub 52, or boss, in an internal area 54 formed by a perimeter 56 edge of the support 14 (see also FIG. 3). As illustrated, the elevated hub 52 has a mesa shape, meaning essentially a substantially flat top with steep sides, not necessarily vertical, though vertical sides can be implemented. The substantially flat top provides a surface to engage with the microneedle patch 38 near a center of the patch, and the steep drop-off of the sides removes the likelihood of any of the support structure interfering with the microneedles of the microneedle array 44. This example configuration directs the microneedles of the microneedle array 44 inward, and suspends the microneedles within the internal area 54, such that they are hidden from a user and not exposed to the environment outside of the microneedle patch support 14. Such an orientation of the microneedle patch 38 and the microneedle array 44 prevents a user from making accidental or unintended contact with the microneedle array 44. A sealing cover 58 (see FIG. 3) can be placed across the support 14 from edge to edge of the perimeter 56, and across the microneedle patch 38, such that the sealing cover 58 applies downward pressure on the microneedle patch 38, holding it against the elevated hub 52, and internal walls of the support along the perimeter 56 prevent the microneedle patch 38 from sliding laterally relative to the elevated hub 52, thus holding the microneedle patch 38 in place and in a sealed configuration. Likewise, the sealing cover 58 can be applied with clearance between the sealing cover 58 and the microneedle patch 38, such that the patch is held substantially in place between the elevated hub 52 (e.g., boss), the sealing cover 58 (e.g., lid), and the perimeter 56. The sealing cover 58 can be adhered to the support 14 using a chemical adhesive, a heat seal, or the like. Such an arrangement lends itself to the maintenance of a sterile environment within which the microneedle patch 38 can be stored until use.

The microneedle patch support 14 further provides sufficient support to hold the microneedle patch 38 in place when the applicator 12 is placed over the microneedle patch support 14 and the support 14 is used to apply a force to the applicator plate 18 and push it into a retracted position. As such, the support 14 must be able to withstand at least a force equivalent to the maximum spring force generated by the compression spring 24 during such a process of retracting the applicator plate 18. Generally, the microneedle patch support 14 may be made of a generally rigid material, including but not limited to, wood, plastic, composite, metal, and the like. A preferred implementation is to form the support 14 of plastic.

In operation, (and looking to FIG. 5) the microneedle patch applicator system 10 of the present invention can be utilized as follows. With the microneedle patch 38 resting on the microneedle patch support 14, the applicator 12 is placed over the support 14 (as shown in FIG. 1) (step 100). The trigger button 35 is depressed (step 102), unlatching the latch mechanism 26 and enabling the sliding movement of the applicator plate 18. The applicator 12 is lowered onto the support 14 until the applicator plate 18 makes contact with the perimeter 56 of the support 14 (step 104). Such action presses the engaging surface 20 of the applicator plate 18 against the support 14 at the perimeter 56 of the support 14.

A downward force applied to the applicator 12 overcomes the spring force of the compression spring 24 and lowers the applicator housing 16, retracting the applicator plate 18. Continued application of the downward force retracts the applicator plate 18 into its fully retracted position, as shown in FIG. 4A. Likewise, when the applicator plate 18 is in its fully retracted position, the docking mechanism 46 engages with the microneedle patch 38 at the aperture 42, in accordance with the example illustrative embodiment. As such, when the applicator plate 18 is in the fully retracted position, the microneedle patch 38 is docked with the applicator 12 (step 106). In addition, once the applicator plate 18 is in its fully retracted position, the trigger button 35 is released and the latch mechanism 26 latches or locks the applicator plate 18 in position (step 108). This is also illustrated in FIG. 4B.

As shown in FIG. 4B, with the latch mechanism 26 holding the applicator plate 18 in the retracted position, the applicator 12 can be lifted off the microneedle patch support 14 (step 110). Because the microneedle patch 38 is docked to the applicator 12, the microneedle patch 38 pulls off of the patch support 14 and stays coupled with the applicator 12 at the docking mechanism 46.

The applicator 12 is then repositioned against a skin surface 50 of a patient (step 112), and the trigger button 35 is depressed to deploy the applicator plate 18 and the microneedle patch 38 (step 114), as shown in FIG. 4C. More specifically, this action unlatches the latch mechanism 26, again allowing sliding movement of the applicator plate 18. With the stored energy of the compression spring 24, the applicator plate 18 is thrust outward (or downward, as illustrated in FIG. 4C) and impacts the skin surface 50 with the microneedle patch 38. The impact force drives the microneedle patch 38, and specifically the microneedle array 44, into the skin surface 50 anchoring the microneedle patch 38 to the skin surface 50 via the adhesive of the microneedle patch 38. If the microneedle patch 38 contains an agent, delivery of such agent begins according to design. The applicator 12 can then be removed from the skin surface 50 (step 116), leaving the microneedle patch 38 anchored/adhered to the skin surface 50. The applicator 12 is then available for future use, repeating the process as described herein, for the application of additional microneedle patches. Accordingly, the applicator 12 of the present invention is reusable. In accordance with one example implementation of the present invention, the applicator 12 can be reused between 30 and 50 times, or more. Each instance of use does require a new microneedle patch to be docked in the applicator 12 and then deployed to the skin surface 50 of a patient.

One of skill in the art will appreciate that with one example intended use of the system 10 being to drive the microneedle array 44 into the skin surface 50 of a patient, it can be necessary to ensure the microneedle patch 38 and the microneedles of the microneedle array 44 are sterile. As such, prior to applying the microneedle patch 38 to the skin surface 50, various processes can be utilized to sterilize the microneedle patch 38 and the microneedle array 44, including but not limited to heat, light, or chemical sterilization processes, including but not limited to heat sterilization, steam sterilization, gamma sterilization, e-beam sterilization, Ethylene Oxide (EtO) sterilization, and the like. Furthermore, components of the device can be individually sterilized and then aseptically assembled. Such sterilization processes are conventional in the art, though their implementation with the particular components of the present system 10 is not. Furthermore, the microneedle patch 38 can be sterilized, together with the microneedle patch support 14, and both components placed and sealed in sterile packaging for storage, or the components can be separately sterilized before being sealed in packaging for shipment or storage. When it is time for application of a microneedle patch 38 to a skin surface 50 of a patient, the microneedle patch 38 coupled with the support 14 can be removed from the sterile packaging by a user, without need for the user to directly handle the microneedle patch 38. Rather, the user can handle only the support 14, thus maintaining the sterility of the microneedle patch 38 and the microneedle array 44. The microneedle patch 38 is then docked to the applicator 12 as described herein, and deployed to the skin surface 50 of a patient, all without anything contacting the microneedles until they impact the skin surface 50.

A package or packages suitable for protecting a drug-loaded microneedle patch, as well as the applicator 12, can be provided to maintain the microneedle patch 38 in a sterile condition prior to use. Suitable packaging protects the microneedle patch 38 from physical/mechanical harm, as well as environment conditions (e.g., moisture, oxygen, other volatiles, etc.), and be a sterile barrier (primary package). Example materials include plastic based materials, including plastic composites and plastic films, metalized plastic films, foil based materials, paper based materials, or synthetic non-woven materials (e.g., flashspun high-density polyethylene fibers) optionally with adhesive (e.g., pressure sensitive adhesive or hot melt adhesive) that in combination provide an airtight an air tight sterile barrier. One of skill in the art will appreciate that a number of different conventional medical device packaging materials meeting these requirements are available for use with the present invention, and therefore further detail of such packaging will not be provided herein.

The agent disposed on the microneedle patch has been defined broadly herein. More specific illustrative examples of such agent include, but are not limited to, therapeutic agents in all the major therapeutic areas including, but not limited to, anti-infectives, such as antibiotics and antiviral agents; analgesics, including fentanyl, sufentanil, remifentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers. These agents may take the form of peptides, proteins, carbohydrates (including monosaccharides, oligosaccharides, and polysaccharides), nucleoproteins, mucoproteins, lipoproteins, glycoproteins, nucleic acid molecules (including any form of DNA such as cDNA, RNA, or a fragment thereof, oligonucleotides, and genes), nucleotides, nucleosides, lipids, biologically active organic or inorganic molecules, or combinations thereof.

Further specific examples of agents include, without limitation, growth hormone release hormone (GHRH), growth hormone release factor (GHRF), insulin, insulotropin, calcitonin, octreotide, endorphin, TRN, NT-36 (chemical name: N-[[(s)-4-oxo-2-azetidinyl]carbonyl]-L-histidyl-L-p-rolinamide), liprecin, pituitary hormones (e.g., HGH, HMG, desmopressin acetate, etc), follicle luteoids, aANF, growth factors such as growth factor releasing factor (GFRF), bMSH, GH, somatostatin, bradykinin, somatotropin, platelet-derived growth factor releasing factor, asparaginase, bleomycin sulfate, chymopapain, cholecystokinin, chorionic gonadotropin, erythropoietin, epoprostenol (platelet aggregation inhibitor), gluagon, HCG, hirulog, hyaluronidase, interferon alpha, interferon beta, interferon gamma, interleukins, interleukin-10 (IL-10), erythropoietin (EPO), granulocyte macrophage colony stimulating factor (GM-CSF), granulocyte colony stimulating factor (G-CSF), glucagon, leutinizing hormone releasing hormone (LHRH), LHRH analogs (such as goserelin, leuprolide, buserelin, triptorelin, gonadorelin, and napfarelin, sexual or reproductive hormones including gonadotropins such as menotropin (including extracted, recombinant and synthetic forms of one or both of urofollitropin (FSH) and LH), oxytocin, streptokinase, tissue plasminogen activator, urokinase, vasopressin, deamino [Val4, D-Arg8] arginine vasopressin, desmopressin, corticotropin (ACTH), ACTH analogs such as ACTH (1-24), ANP, ANP clearance inhibitors, angiotensin II antagonists, antidiuretic hormone agonists, bradykinn antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, parathyroid hormone (PTH), PTH analogs such as PTH (1-34), prostaglandin antagonists, pentigetide, protein C, protein S, renin inhibitors, thymosin alpha-1, thrombolytics, TNF, vasopressin antagonists analogs, alpha-1 antitrypsin (recombinant), and TGF-beta.

The agent can be in various forms, including free bases, acids, charged or uncharged molecules, components of molecular complexes or nonirritating, pharmacologically acceptable salts. Further, simple derivatives of the agent (such as ethers, esters, amides, etc.), which are easily hydrolyzed at body pH, enzymes, etc., can be employed.

Additional agents may be included. For example, the agent may include a viscosity enhancing agent, such as maleic acid, malic acid, malonic acid, tartaric acid, adipic acid, citraconic acid, fumaric acid, glutaric acid, itaconic acid, meglutol, mesaconic acid, succinic acid, citramalic acid, tartronic acid, citric acid, tricarballylic acid, ethylenediarninetetraacetic acid, aspartic acid, glutamic acid, carbonic acid, sulfuric acid, phosphoric acid, hydrochloric acid, hydrobromic acid, nitric acid, sulfuric acid, benzene sulfonic acid, methane sulfonic acid, glycolic acid, gluconic acid, glucuronic acid, lactic acid, pyruvic acid, tartronic acid, propionic acid, pentanoic acid, carbonic acid, adipic acid, citraconic acid, and levulinic acid.

Additional potential agents include surfactants, such as zwitterionic, amphoteric, cationic, anionic, or nonionic, including, without limitation, sodium lauroamphoacetate, sodium dodecyl sulfate (SDS), cetylpyridinium chloride (CPC), dodecyltrimethyl ammonium chloride (TMAC), benzalkonium, chloride, polysorbates such as Tween 20 and Tween 80, other sorbitan derivatives, such as sorbitan laurate, and alkoxylated alcohols, such as laureth-4.

Still other useful agents include polymeric materials or polymers that have amphiphilic properties, for example and without, cellulose derivatives, such as hydroxyethylcellulose (HEC), hydroxypropylmethylcell--ulose (HPMC), hydroxypropylcellulose (HPC), methylcellulose (MC), hydroxyethylmethylcellulose (HEMC), or ethylhydrox-ethylcellulose (EHEC), as well as pluronics.

Further agents include biocompatible carriers, which include, without limitation, human albumin, bioengineered human albumin, polyglutamic acid, polyaspartic acid, polyhistidine, pentosan polysulfate, polyamino acids, sucrose, trehalose, melezitose, raffinose and stachyose.

Agents can further include stabilizing agents, which can comprise, without limitation, a non-reducing sugar, a polysaccharide or a reducing sugar. Suitable non-reducing sugars include, for example, sucrose, trehalose, stachyose, or raffinose. Suitable polysaccharides include, for example, dextran, soluble starch, dextrin, and insulin. Suitable reducing sugars include, for example, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose, and the like.

Other agents include "pathway patency modulators", which can comprise, without limitation, osmotic agents 202 (e.g., sodium chloride), zwitterionic compounds (e.g., amino acids), and anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

Further agents include a solubilising/complexing agent, for example, alpha-cyclodextrin, beta-cyclodextrin, gamma-cyclodextrin, glucosyl-alpha-cyclodextrin, maltosyl-alpha-cyclodextrin, glucosyl-beta-cyclodextrin, maltosyl-beta-cyclodextrin, hydroxypropyl beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-alpha-cyclodextrin, sulfobutylether-beta-cyclodextrin, sulfobutylether7 beta-cyclodextrin, and sulfobutylether-gamma-cyclodextrin.

Additional useful agents include non-aqueous solvents, such as ethanol, isopropanol, methanol, propanol, butanol, propylene glycol, dimethysulfoxide, glycerin, N,N-dimethylformamide and polyethylene glycol 400.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A microneedle patch applicator, comprising:
   a housing;
   a slidably disposed applicator plate, moveable between a retracted position and a deployed position in a reciprocating manner, the applicator plate having an engaging surface and the applicator plate having a cylindrical aperture that passes therethrough, the cylindrical aperture having an internal wall;
   a spring mounted in such a way that imparts a spring force to the applicator plate when the applicator plate is in the retracted position;

a microneedle patch docking mechanism configured in such a way that the docking mechanism captures and holds a microneedle patch in a position proximal the engaging surface of the applicator plate while the applicator plate is in the retracted position; and a latch mechanism that frictionally engages with the internal wall of the cylindrical aperture to hold the applicator plate in place, and when unlatched disengages from the internal wall and permits the applicator plate to move;

wherein the applicator plate is placed in the retracted position with the docking mechanism holding the microneedle patch proximal the engaging surface, and when the latch mechanism is unlatched, the applicator plate is propelled by the spring to the deployed position.

2. The microneedle patch applicator of claim 1, further comprising a trigger mechanism configured in such a way that activation of the trigger unlatches the latch mechanism.

3. The microneedle patch applicator of claim 1, wherein when the latch mechanism is in an unlatched position, the applicator plate is capable of retraction to the retracted position in response to a force applied to the microneedle patch applicator.

4. The microneedle patch applicator of claim 1, wherein unlatching of the latch mechanism when the applicator plate is in the retracted position releases the applicator plate enabling movement from the retracted position to the deployed position with a kinetic energy of between about 0.1 lbf*in and about 10 and preferably between about 1 lbf*in and about 2 lbf*in.

5. The microneedle patch applicator of claim 1, wherein the spring has a spring constant of between about 0.1 lbf/in and about 50 lbf/in, and preferably between about 2.4 and about 8.5 lbf/in.

6. The microneedle patch applicator of claim 1, wherein the microneedle patch applicator deploys the microneedle patch with sufficient force to anchor the microneedle patch to a skin surface with a plurality of microneedles disposed thereon.

7. The microneedle patch applicator of claim 1, wherein the microneedle patch applicator is stored in a sterile packaging prior to use.

8. The microneedle patch applicator of claim 1, wherein the spring comprises a compression spring.

* * * * *

UNITED STATES PATENT AND TRADEMARK OFFICE
CERTIFICATE OF CORRECTION

| | |
|---|---|
| PATENT NO. | : 8,734,395 B2 |
| APPLICATION NO. | : 13/972442 |
| DATED | : May 27, 2014 |
| INVENTOR(S) | : McAllister |

Page 1 of 1

It is certified that error appears in the above-identified patent and that said Letters Patent is hereby corrected as shown below:

In the Claims:

Column 14, claim 4, line 6, "10" should read "10 lbf*in".

Signed and Sealed this
Twenty-third Day of September, 2014

Michelle K. Lee
*Deputy Director of the United States Patent and Trademark Office*